United States Patent [19]

Fukunaga et al.

[11] 3,932,534

[45] Jan. 13, 1976

[54] PROCESS FOR HYDROGENATION REACTION OF UNSATURATED ORGANIC COMPOUNDS

[75] Inventors: Yasuhisa Fukunaga, Takamatu; Akira Okada, Takamatu, both of Japan

[73] Assignee: Kyowa Kagaku Kogyo Kabushiki Kaishi, Tokyo, Japan

[22] Filed: June 8, 1973

[21] Appl. No.: 368,327

[30] Foreign Application Priority Data

June 8, 1972 Japan.................. 47-56501

[52] U.S. Cl. ............ 260/618 H; 252/441; 252/442; 252/461; 252/470; 260/268 SY; 260/293.52; 260/409; 260/563 C; 260/563 D; 260/583 K; 260/621 H; 260/631 H; 260/632; 260/638 A; 260/638 B; 260/667 H; 260/676 R; 260/683.9; 260/690

[51] Int. Cl.² .............. C07C 33/06; C07C 31/02; C07C 31/16

[58] Field of Search .................. 260/618 H, 638 B

[56] References Cited

UNITED STATES PATENTS

| | | | |
|---|---|---|---|
| 1,684,640 | 9/1928 | Schmidt et al. | 260/638 B |
| 2,009,948 | 7/1935 | Schmidt et al. | 260/638 B |
| 2,093,159 | 9/1937 | Schmidt | 260/638 A |
| 2,334,100 | 11/1943 | Ipatieff et al. | 260/618 H X |

*Primary Examiner*—Donald G. Daus
*Assistant Examiner*—D. B. Springer
*Attorney, Agent, or Firm*—Sherman & Shalloway

[57] ABSTRACT

When a solid reduction catalyst prepared by calcining and reducing at 350° to 700°C. in a hydrogen stream a precursor compound having a composition expressed by the following formula $$M_xNi_yAl_z(OH)_{2x+2y+cz-tp}(A)_p \cdot aH_2O$$

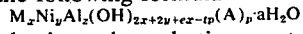

and having a layer lattice crystal structure characterized by the following X-ray diffraction pattern

| d (A) | I/Io |
|---|---|
| 7.5–210.2 | 100 |
| 3.6–10.6 | 5 – 80 |
| 2.4–6.4 | 5 – 60 | is employed for hydrogenation reduction of unsaturated organic compounds, the intended reduction products can be obtained at very high conversion and very high selectivity.

11 Claims, 5 Drawing Figures

PROCESS FOR HYDROGENATION REACTION OF UNSATURATED ORGANIC COMPOUNDS

This invention relates to an improvement in the process for hydrogenation reduction of compounds having a multiple bond between a carbon atom and an atom selected from the group consisting of carbon, oxygen, sulfur and nitrogen, such as C=C, C≡C, C=O, C=N and C≡N.

Various solid reduction catalysts such as Ni-diatomaceous earth, Raney nickel, Ni—$Al_2O_3$ (carrier), Cu-Ni and Cu-diatomaceous earth have heretofore been used for hydrogenation reduction of aromatic compounds, aldehydes, ketones, nitriles and the like. According to the conventional theory, the particle size (so called X-ray particle size determined by the X-ray diffractiometry) of metallic nickel used as the catalyst component is considered to exert a great influence on the activity and selectivity of the catalyst, and it is said that a catalyst having a smaller X-ray particle size has a more improved activity. Particle sizes of nickel in conventional nickel-type hydrogenation reduction catalysts are disclosed in various literature references. For instance, Harshaw Keoing Walter, "Catalyst, 13 (4), 1579 (1971)" and Kishida and Adachi, "Kogyo Kagaku Zasshi, 74 (11), 2398 (1971)" disclose the following particle sizes:

| | |
|---|---|
| Raney nickel catalyst | 50 to 120 A |
| Raney type Cu-Ni alloy | 66 to 134 A |
| reduced nickel catalyst | 100 to 700 A |

We have now found that a catalyst formed by employing as a catalyst precursor a layer lattice crystal substance composed of a composite metal hydroxide of the Ni—Al system or the Ni—Mg system, and reducing and calcining this precursor in a hydrogen stream is advantageous over the conventional nickel-type reduced catalyst for hydrogenation reduction in the point that the increase of the X-ray particle size by calcination under heat is smaller and the particle size distribution is more uniform. It has also been found that the so formed catalyst has a desired combination of a good thermal stability and an excellent activity and this catalyst is very effective for hydrogenation reduction of unsaturated organic compounds such as mentioned above.

It is a primary object of this invention to provide a process for hydrogenation reduction of unsaturated organic compounds with use of a novel nickel-type catalyst.

Another object of this invention is to provide a process for hydrogenation reduction of unsaturated organic compounds, in which the X-ray particle size of the nickel component of the catalyst used is much smaller than that in the conventional nickel-type hydrogenation catalysts and hence, the intended hydrogenation reduction product can be obtained at a high selectivity and a high conversion Still another object of this invention is to provide a process in which a catalyst for hydrogenation reduction having constant activity and selectivity can be obtained by employing as a catalyst precursor a compound having a stable layer lattice crystal structure, and the hydrogenation reduction treatment can be accomplished stably on an industrial scale by employing such catalyst.

In accordance with this invention, there is provided a process for hydrogenation reduction of unsaturated organic compounds which comprises reducing with hydrogen an unsaturated organic compound having a multiple bond between a carbon atom and an atom selected from the group consisting of carbon, oxygen, sulfur and nitrogen in the presence of a solid catalyst for reduction, such solid catalyst obtained by calcining and reducing at a temperature of 350° to 700°C. in a hydrogen stream a compound having a composition expressed by the following general formula $$M_rNi_uAl_z(OH)_{2x+2y+3z-tp}(A)_p \cdot aH_2O$$

wherein A stands for an anion, M stands for magnesium and/or zinc, $t$ designates the valency of the anion A and $x$, $y$, $z$, $p$ and $a$ are such numbers that when $z$ is 2, the following relations are established:

$x + y = 0.1$ to 20,
$x = 0$ to 19.9, and
$y = 0.1$ to 20, and the following conditions are satisfied:

$1/6 > p/(x + y + z) > 1/20$, and
$a > 0$ and having substantially the following diffraction pattern in the powder X-ray diffractiometry (Cu-Kα):

| d (A) | I/Io |
|---|---|
| 7.5 – 21.02 | 100 |
| 3.6 – 10.6 | 5 – 80 |
| 2.4 – 6.4 | 5 – 60 |

This invention will now be described in detail.

Catalyst

Since the novel nickel type catalyst to be used in the process of this invention is prepared from a precursor substance having a layer lattice crystal structure which is composed of a composite metal hydroxide of the Ni—Al, Ni—Mg—Al, Ni—Zn—Al or Ni—Mg—Zn—Al system, the novel catalyst of this invention is characterized in that it has a smaller X-ray particle size of nickel than known nickel type catalysts and it exhibits higher catalytic activity and higher selectivity than known nickel type catalysts.

X-ray particle sizes [determined with respect to face (111)] and specific surface areas of catalysts formed from Ni—Al coprecipitate precursors prepared by a known method (catalysts of Comparative Examples 1 and 2 given hereinafter) and catalysts prepared by employing as precursors composite metal hydroxides of the Ni—Al, Ni—Mg—Al, Ni—Zn—Al and Ni—Zn—Mg—Al systems having a layer lattice crystal structure specified in this invention are shown in Table 1.

Table 1

| Precursor No. | Composition Formula of Precursor | Calcining and Reducing Conditions | BET Specific Surface Area (m²/g) of Catalyst | X-Ray Particle Size (A) [(111) face] of Catalyst |
|---|---|---|---|---|
| 1 | $Ni_{2.7}Mg_{2.3}Al_2(OH)_{16.7}(CO_3)_{0.7}$ | I* | 315 | too fine and immesurable |
| | | II* | 299 | too fine and immesurable |
| 2 | $Ni_{0.5}Mg_{2.3}Al_2(OH)_{10.6}(CO_3)_{0.58}$ | I | 290 | too fine and immesurable |
| | | II | 368 | too fine and immesurable |

Table 1-continued

| Precursor No. | Composition Formula of Precursor | Calcining and Reducing Conditions | BET Specific Surface Area (m²/g) of Catalyst | X-Ray Particle Size (A) [(111) face] of Catalyst |
|---|---|---|---|---|
| 3 | $Ni_{10}Mg_3Al_2(OH)_{30}(NO)_{3.1}$ | I | 281 | about 23 |
|   |   | II | 271 | 30 |
| 4 | $Ni_8Al(OH)_8(NO_3)_{1.1}$ | I | 210 | 34 |
|   |   | II | 89 | 72 |
| 5 | $Ni_{0.57}Al(OH)_{3.9}(CO_3)_{0.26}$ | I | 326 | too fine and immesurable |
|   |   | II | 230 | about 22 |
| 6 | $Ni_{0.1}Mg_{3.2}Zn_{3.0}Al_2(OH)_{16.4}(C_2O_4)_{1.1}$ | I | 157 | too fine and immesurable |
|   |   | II | 138 | too fine and immesurable |
| 7 | $Ni_{3.4}Zn_{1.7}Al_2(OH)_{14}(CO_3)_{1.1}$ | I | 131 | too fine and immesurable |
|   |   | II | 109 | about 25 |
| Comparative Example 1 | Ni-Al coprecipitate (Ni/Al = 0.07) | I | 219 | about 24 |
|   |   | II | 52 | 98 |
| Comparative Example 2 | Ni-al coprecipitate (Ni/Al = 0.35) | I | 221 | about 29 |
|   |   | II | 79 | 73 |

Notes:
*hydrogen flow rate = 12 1/hr, 400°C. × 2 hours
**hydrogen flow rate = 12 1/hr, 450°C. × 2 hours From Table 1, it is seen that with due regard to the nickel content, the conditions for reducing and calcining the catalyst precursor and other factors, in the catalyst to be used in this invention the X-ray particle size of nickel is apparently smaller than in the nickel type catalyst of the similar kind. In general, in the catalyst of this invention the X-ray particle size is within the range not exceeding 60 A. It is believed that the reason why the X-ray particle size in the catalyst of this invention is much smaller than that in the conventional catalysts obtained by employing precursors formed by the known coprecipitation method or oxalate method, when compared besed on the same composition, is that in the composite metal hydroxide of the Ni—Al, Ni—Mg—Al, Ni—Zn—Al or Ni—Zn—Mg—Al system having a layer lattice crystal structure specified in this invention, as will be detailed hereinafter, nickel hydroxide units are combined finely and uniformly into the crystal structure. By dint of this structural characteristics of the precursor, the catalyst of this invention can possess a fine X-ray particle size, active points uniformly distributed in the catalyst and a high thermal stability. As a result, the catalyst of this invention makes it possible to perform the hydrogenation reduction of unsaturated organic compounds at high conversion and high selectivity. These excellent effects attained by the catalyst of this invention will be readily understood from the accompanying drawings, in which:

Figure 1:
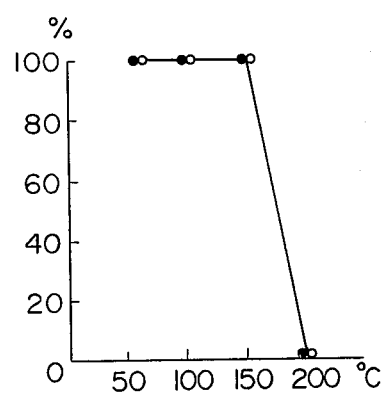
FIG. 1 is a curve illustrating the relation of the reaction temperature to the conversion and selectivity in the hydrogenation reduction conducted by using the catalyst of Example 3.

The catalyst of this invention is of two-to-four components and contains aluminum, magnesium and/or zinc, and nickel at the following atomic ratio:
Al : (Mg + Zn) : Ni = 2 : (0 to 19.9) : (0.1 to 20)

In the above catalyst, it it believed that the aluminum component, the zinc component and the magnesium component are present in the form of oxides or hydroxides, and the nickel component is present partially in the metallic form and partially in the form of the oxide. In this catalyst, as the nickel content is higher and the content of zinc or magnesium is lower, the X-ray particle size of nickel in the catalyst is generally larger. Accordingly, in order to obtain a high catalytic activity in this invention, it is preferred to employ a catalyst having a relatively low nickel content and a relatively high content of magnesium or zinc. However, in the catalyst of this invention the X-ray particle size is generally less than 60 A, as far as the atomic ratio of the metals is within the above-mentioned range.

The precursor to be used for the preparation of the catalyst of this invention is a layer lattice crystal substance which is expressed by the following formula
$$M_xNi_yAl_2(OH)_{2x+2y+3z-tp}(A)_p \cdot aH_2O \quad (*)$$

wherein A stands for an anion, M stands for magnesium and/or zinc, $t$ designates the valency of the anion A, and $x$, $y$, $z$, $p$ and $a$ are such numbers that when z is 2, the following relations are established:
$x + y = 0.1$ to 20,
$x = 0$ to 19.9, and
$y = 0.1$ to 20,
and the following conditions are satisfied:
$1/20 < p/(x+y+z) < 1/6$, and
$a > 0$ and has substantially the following diffraction pattern in the powder X-ray diffractiometry (Cu-Kα):

| d(A)(spacing) | I/Io (relative intensity) |
|---|---|
| 7.5 – 21.02 | 100 |
| 3.6 – 10.6 | 5 – 80 |
| 2.4 – 6.4 | 5 – 60 |

As a result of the X-ray diffractiometry, the differential thermal analysis, the thermogravimetric analysis, the infrared absorption spectrum analysis and the like, it was confirmed that the above crystal substance contains water of crystallization in the state inserted in the sandwich form between layer lattices and it is characterized by a lattice constant of $a_0 = 3.1$ A and $d = 45$ to 132 A.

From the X-ray diffraction pattern it is seen that in the above crystal substance, though spacings $d$ of faces (006), (0012) and (0018) vary depending on the kind of the anion, changes in other faces are very small. Accordingly, identification of this crystal substance can easily be done by examining the pattern of the region in which the value of $d$ is not greater than 2.31 A and confirming the changes of $d$ on faces (006), (0012) and (0018).

In the precursor of the above composition formula, the anion A can be 1 to 4 inorganic or organic anions. As the inorganic anions, there may be mentioned, for example, halide ions such as $Cl^-$ $Br^-$ and $I^-$, halogen oxyacid ions such as $ClO_2^-$, $ClO^-$ and $ClO_3^-$, and oxyacid ions of such atoms as carbon, nitrogen, sulfur, phosphorus and arsenic (acidic oxide anions), such as carbonic acid ion, nitric acid ion, sulfuric acid ion and phosphoric acid ion. As the organic anion, there may be mentioned ions of carboxylic acids such as formic acid, oxalic acid, acetic acid, glycolic acid, succinic acid and tartaric acid. In view of the activity of the resulting catalyst, it is preferred that the anion of the precursor to be used in this invention has such a property that it can decompose or be released at the reducing treatment conducted for obtaining the intended catalyst. From this viewpoint, halide ions, nitric acid ion, carbonic acid ion, formic acid ion and oxalic acid ions are preferred as the anion A. Nitric and carbonic acid ions are especially preferred.

The fundamental form of this novel composite metal hydroxide is expressed by the following general formula $$Ni_mM_nAl_2(OH)_{16}\cdot A_{k}\cdot a'H_2O \qquad (2)$$

wherein A and M are as defined above, $m$ and $n$ are numbers satisfying the following conditions:
$m = 1$ to 6,
$n = 0$ to 5, and
$m + n = 6$,
$k$ is 2 when A is a monovalent anion or $k$ is 1 when A is a divalent anion, and
$a'$ is a number of from 2 to 5.

In this novel composite metal hydroxide, Ni or (Ni + Mg + Zn) forms a mixed crystal with Al within such a range that the atomic ratio of Ni or (Ni + Mg + Zn) to Al is maintained at a certain level, namely within the following range:

$$\tfrac{1}{4} \leq (x + y)/z \leq 8$$

This can be readily understood from the fact that when the above composite metal hydroxides are prepared by varying the ratio of (Ni + Mg + Zn) to Al and the resulting products are analyzed by the X-ray diffractiometry, there is established a substantially proportional relation between the lattice constant on the face (006) and the mole ratio of (Ni + Mg + Zn)/[(Ni + Mg + Zn) + Al] and the Vegard law holds good in these products. This crystal structure consists of layers formed by ol-linkages between $Al(OH)_3$, and $Ni(OH)_2$ or $Ni(OH)_2$ and $Mg(OH)_2$ or $Zn(OH)_2$ and intermediate layers composed of coordination anions and water molecules, and $Ni(OH)_2$, or $Ni(OH)_2$ and $Mg(OH)_2$ or $Zn(OH)_2$ form a hexadentate octahedron layer together with $Al(OH)_3$. It is believed that the coordination anion A is positioned almost rectangularly to such octahedron layer and connects two octahedron layers. From the foregoing description it will readily be understood why the X-ray particle size of nickel is very fine in the catalyst of this invention.

Generally speaking, the composite metal hydroxide of the above formula (1) is prepared by reacting (i) $y$ moles of a divalent nickel compound, (ii) $x$ moles of a magnesium compound and/or a zinc compound and (iii) $z$ moles of an aluminum compound in the presence of water and an anion A at a pH of at least 6.5, especially at least 8.0 when the metal M is Mg, at least 6.5 when M is Zn or at least 6.5 when M is mixture of Zn and Mg, for a time enough to obtain a composite metal hydroxide having the above-mentioned specific layer lattice crystal structure.

As the divalent nickel compound, there may be employed compounds expressed by the following formula $$NiX_{2/q} \qquad (3)$$

wherein X stands for an inorganic anion and q designates the valency of the anion X.

Examples of compounds expressed by the above formula (3) are nickel (II) chloride, nickel (II) bromide, nickel (II) nitrate and nickel (II) sulfate.

As the magnesium compound, there may be employed compounds expressed by the following formula $$MgX_{2/q} \qquad (4)$$

wherein X and $q$ are as defined above.

Examples of such magnesium compounds are magnesium chloride, magnesium bromide, magnesium nitrate, magnesium sulfate, magnesium carbonate, basic magnesium carbonate and magnesium oxide.

As the zinc compound, there may be employed compounds expressed by the following formula $$ZnX_{2/q} \qquad (5)$$

wherein X and $q$ are as defined above.

Examples of such zinc compounds are zinc chloride, zinc nitrate and zinc sulfate.

As the aluminum compound, there may be employed aluminum compounds expressed by the following formula $$AlY_{3/q'} \qquad (6)$$

wherein Y stands for an inorganic anion or a lower alkoxy group and $q'$ designates the valency of Y. and alkali metal aluminates. More specifically, there can be preferably used aluminum chloride, aluminum bromide, aluminum nitrate, aluminum sulfate, aluminum ethoxide, aluminum isopropoxide, aluminum hydroxide, sodium aluminate, potassium aluminate and the like.

The anion A to be combined into the composite metal hydroxide and the anion X or Y of the starting compound may be the same or different. For instance, when a halide ion or nitric radical is combined into the composite metal hydroxide, compounds including such anion can be used as the starting compound. Further, in case a carbonic acid ion is combined into the composite metal hydroxide, the carbonic acid ion which is different from anions of the starting compounds can be added in the form of an alkali metal carbonate or alkali metal bicarbonate or by saturating the reaction system with carbon dioxide gas.

The following cares should be taken in conducting the above reaction of forming the composite metal hydroxide of the formula (1):

a. In case a monovalent ion such as a halide ion, a nitric acid ion, a formic acid ion or the like is combined into the composite metal hydroxide, no divalent anion should be present in the reaction system.

b. In case a divalent anion other than a carbonic radical, for example, an oxalic acid ion, is combined into the composite metal hydroxide, no carbonic acid ion should be present in the reaction system. Of course, a mixture of monovalent and divalent anions or a mixture of these anions with a carbonic acid anion may be combined in the composite metal hydroxide in this invention, and no particular disadvantage is brought about in this invention when such anions are combined in the mingled state into the composite metal hydroxide.

In general, it is preferred that the reaction is carried out in water at a pH of at least 8, especially at least 9. The reaction temperature is from room temperature to about 350°C. The reaction may be performed under atmospheric pressure and pressurization is effected suitably depending on the reaction temperature. It is possible to subject the resulting composite metal hydroxide to a post treatment comprising immersing the composite hydroxide into water and heating it under pressure. By this post treatment, the degree of crystallinity is further improved in the composite metal hydroxide.

One of preferred precursors to be used in this invention is a composite metal hydroxide in which the atomic ratio of (Mg and/or Zn) : Ni : Al is (0 to 6) : (0.2 to 10) : 2, especially (0 to 4.5) : (0.5 to 2) : 2.

Another preferred precursor to be used in this invention is a composite metal hydroxide expressed by the following formula $$Ni_yAl_2(OH)_{6+2y-tp}(A)_p \cdot aH_2O$$

wherein A is a nitric acid ion, a formic acid ion, an oxalic acid ion or a carbonic acid ion, $y$ is a number of from 0.1 to 6, $t$ designates the valency of the anion A, $a$ is a positive number, and $p$ is a number satisfying the condition of $1/6 > p/(2+y) > 1/20$.

Still another preferred precursor to be used in this invention is a composite metal hydroxide expressed by the following formula $$Ni_yMg_xAl_2(OH)_{6+2y+2x-tp}(A)_p \cdot aH_2O$$

wherein A is a nitric acid ion, a formic acid ion, an oxalic acid ion or a carbonic acid ion, $y$ is a number of from 0.1 10, $x$ is a number of from 1.5 to 5.5, $t$ designates the valency of the anion A, $a$ is a positive number, and $p$ is a number satisfying the condition of $1/6 > p/(2+x+y) > 1/20$.

A still further example of preferred precursors to be used in this invention is a composite metal hydroxide expressed by the following formula $$Ni_yZn_xAl_2(OH)_{6+2y+2z-tp}(A)_p \cdot aH_2O$$

wherein A is a nitric acid ion, a formic acid ion, an oxalic acid ion or a carbonic acid ion, $y$ is a number of from 0.1 to 10, $x$ is a number of from 1.5 to 5.5, $t$ designates the valency of the anion A, $a$ is a positive number and $p$ is a number satisfying the condition of $1/6 > p/(2+x+y) > 1/20$.

A still further example of preferred precursors to be used in this invention is a composite metal hydroxide expressed by the following formula $$Ni_yZn_{x'}Mg_{x''}Al_2(OH)_{6+2y+2x'+2x''-tp}(A)_p \cdot aH_2O$$

wherein A is a nitric acid ion, a formic acid ion, an oxalic acid ion or carbonic acid ion, $y$ is a number of from 0.1 to 10, $x'$ and $x''$ each stand for a number of from 1.5 to 5.5, $t$ designates the valency of the anion A, $a$ is a positive number, and $p$ is a number satisfying the conditions of $1/6 > p/(2+y+x'+x'') > 1/20$.

The catalyst precursor composed of such a composite metal hydroxide as illustrated hereinabove is calcined and reduced to obtain a final catalyst.

In this invention, it is generally preferred that a pretreatment for removing water of crystallization from the catalyst precursor is conducted prior to the calcining and reducing treatment.

In this pretreatment, the precursor substance is treated at a temperature of 80° to 250°C. to remove water of crystallization therefrom. Sufficient results can be obtained by conducting the heating under atmospheric pressure, but when it is desired to remove water of crystallization quickly, it is possible to conduct the heating under reduced pressure. In order to remove generated water as quickly as possible from the system, it is desired to conduct the heating pretreatment under ventilation. The time for this pretreatment is not particularly critical, and all of water of crystallization should not necessarily be removed at this pretreatment. After this water-removing pretreatment, the so treated product is calcined at a temperature of 300° to 700°C. Air can be used as an atmosphere for calcination, and in order to remove water generated during the calcining treatment, it is preferable to conduct the operation while passing such a fluid as heated air through the calcination system. The calcination is generally carried out at a temperature of 300° to 700°C., preferably from 400° to 500°C. The calcination time is varied to some extent depending on the calcination temperature and the amount to be treated, and a suitable time condition may be so selected that dehydration is substantially completed.

By the above-mentioned pretreatments, the catalyst precursor composed of a composite metal hydroxide is dehydrated and converted to a dehydrated hydroxide or oxide, but under microscopic observation it still retains the crystal framework and its BET specific surface area is greater than those of oxides formed by known methods.

According to this invention, the so formed polyatomic oxide or hydroxide is calcined and reduced in a hydrogen stream at a temperature ranging from 350° to 700°C., preferably 400° to 500°C. By this calcining and reducing treatment, nickel oxide is reduced to metallic nickel. At this treatment, all of nickel oxide should necessarily be reduced to metallic nickel, but only a part of nickel oxide may be reduced to metallic nickel to form a mixture of nickel oxide (NiO) and metallic nickel. For instance, if the treatment is conducted under such conditions as will give only metallic nickel, sintering of crystals of metallic nickel proceeds and the particle size of metallic nickel becomes greater, with the result that the resulting catalyst is adversely affected with respect to the activity and selectivity and it is not suitable for attaining the objects of this invention. In this invention, it is considered that good results are obtained when the reduction ratio of nickel oxide (NiO) to metallic nickel is 3 to 70%, especially 15 to 70%. In other words, it is preferred that the mole ratio of NiO : Ni is within a range of from 30 : 70 to 97 : 3, especially from 30 : 70 to 85 : 15.

If the calcining and reducing treatment is conducted under such conditions as will reduce nickel oxide to metallic nickel within the above range, fulfilment of any other condition is not required. However, in case the calcining and reducing treatment is conducted at high temperatures for a long time, it sometimes happens that the X-ray particle size of metallic nickel in the catalyst becomes too great and defects such as mentioned above are brought about. Accordingly, in such case cares should be taken so as to prevent occurrence of such undesired phenomenon.

In preparing the catalyst to be used in this invention, it is possible to omit the above-mentioned water-removing pretreatment conducted at 100° to 250°C. and the dehydration calcination treatment conducted at 300° to 700°C. and to directly calcine and reduce the above-mentioned precursor substance in a hydrogen stream at a temperature of from 350° to 700°C.

The novel catalyst to be used in this invention can be obtained by the foregoing procedures, and this catalyst may be stabilized by a known method, if desired. For instance, this catalyst is treated in an inert gas atmosphere containing a small amount of oxygen at such a temperature as will not cause a substantial growth of particles of nickel oxide and metallic nickel in the catalyst. In this case, it is generally preferred that the oxygen content in the treating atmosphere gas is 0.2 to 2%, and from the industrial view point it is preferable to employ nitrogen as the inert gas. It is generally desired that the treatment is carried out at 50° to 200°C.

The treatment for calcining and reducing the catalyst precursor and optional water-removing and stabilizing treatments can be conducted prior to the hydrogenation reduction of unsaturated organic compounds in vessels different from the reaction vessel for the hydrogenation reduction. It is also possible to conduct such treatments in the reaction vessel for the hydrogenation reduction by charging the catalyst precursor or its dehydrated product into the reaction vessel prior to the hydrogenation reduction.

As described hereinabove, a hydrogenation reduction catalyst in which the X-ray particle size of the nickel component is very fine is obtained in this invention by using as a catalyst precursor a novel composite metal hydroxide having a specific layer lattice crystal structure. This catalyst of this invention exhibits much higher activity and selectivity than conventional catalysts obtained by calcining coprecipitate hydroxides, oxalates or carbonates, when the comparison is made based on the same composition. Further, it will be understood that advantages and effects attained by the catalyst of this invention cannot at all be attained by these conventional catalysts.

The catalyst of this invention can be used in the as-prepared form for the hydrogenation reduction, but it may be used, if desired, in the form supported on a known carrier such as alumina, silica, alumina-silica, amorphous silicate, crystalline silicate or the like.

Hydrogenation Reduction Step

The process of this invention is effective for hydrogenation reduction of various unsaturated organic compounds having such unsaturated bonds as C=C, C ≡ C, C=O, C=N, C ≡ N and the like. As such unsaturated organic compound, there may be mentioned, for example, aromatic hydrocarbons, ethylenically unsaturated hydrocarbons, acetylenic hydrocarbons, and their alcohol, phenol and amine derivatives; aldehydes, ketones and esters; nitrogen-containing unsaturated heterocyclic compounds and nitriles; and the like.

Preferred examples of the hydrogenation reduction of these compounds are described below:

1. Nuclear Hydrogenation of Aromatic Hydrocarbon Compounds:

Nuclear hydrogenation of aromatic hydrocarbons such as benzene, toluene, xylene, naphthalene, diphenyl and anthracene; aromatic amines such as aniline, phenylene diamine and xylylene diamine; phenols such as phenol and hydroquinone; and aromatic alcohols such as xylene glycol.

2. Hydrogenation of Olefinic Hydrocarbons and Acetylenic Hydrocarbons:

Hydrogenation of iso-octene, cyclo-octatriene, cyclododecatriene, cinnamic alcohol and the like, selective hydrogenation of acetylenes in cracked gasoline and other petroleum hydrocarbon cracked products to mono-olefines, selective hydrogenation of diolefins to mono-olefins, and hardening of animal oils and fats and vegetable oils and fats.

3. Hydrogenation Reduction of Aldehydes, Ketones and Esters to Alcohols:

Hydrogenation reduction of carbonyl compounds of the following formula

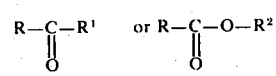

wherein R is an alkyl or aralkyl group having up to 12 carbon atoms, $R^1$ is a hydrogen atom or the group R, and $R^2$ is a lower alkyl group having up to 4 carbon atoms, such as acetone, methylethylketone, butylaldehyde, phenylacetaldehyde and ethyl phenylacetate, to alcohols expressed by the following formula

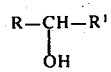

wherein R and $R^1$ are as defined above,
and reduction of oils and fats to higher alcohols.

4. Reduction of Nitrogen-Containing Unsaturated Heterocyclic Compounds to Nitrogen-Containing Saturated Heterocyclic Compounds:

Reduction of pyridine, pyrazine and the like to piperidine, piperazine and the like.

5. Reduction of Nitriles to Amines:

Reduction of nitriles expressed by the following formula

wherein $R^3$ is a monovalent hydrocarbon radical having up to 16 carbon atoms, especially alkyl groups, and $R^4$ is a divalent hydrocarbon radical having up to 16 carbon atoms, especially alkylene groups, such as succinonitrile, adiponitrile, sebacinitrile, 1,10-decane dinitrile and 1,12-dodecane dinitrile, to amines expressed by the following formula

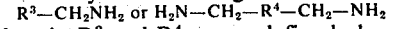

wherein $R^3$ and $R^4$ are as defined above.

The hydrogenation reduction according to this invention is conducted under known catalytic reduction conditions except that the above-mentioned novel catalyst is employed.

For instance, a gas phase method comprising passing a vapor of the starting substance together with a hydrogen gas on a heated catalyst, and a liquid phase method comprising shaking or agitating a liquid phase comprising the starting substance, a catalyst and, if desired, a solvent while passing a hydrogen gas therethrough, can be adopted in this invention. A suitable hydrogenation reduction method is chosen depending on the kind of the starting substance. The reaction temperature is varied considerably depending on the kind of the substance to be reduced and the desired degree of reduction, but it is generally preferred that the reaction is carried out at temperatures ranging from room temperature to 250°C, especially 50° to 200°C. The hydrogen pressure to be employed is also varied considerably depending on the kind of the substance to be reduced, the desired degree of reduction and the reaction temperature. For instance, an atmospheric pressure method employing hydrogen under atmospheric pressure and a high pressure method using hydrogen maintained under up to about 500 Kg/cm$^2$ can be adopted in this invention.

The reaction can be performed either continuously or batchwise. In the continuous method, for instance, a high pressure reaction column is employed, and in the batchwise method an autoclave is employed. Known solvents such as water, alcohols, e.g., ethanol, and ethers, e.g., diethyl ether and tetrahydrofuran can be used for the catalytic reduction conducted in the liquid phase.

A prominent advantage that the intended reduction product can be obtained at high selectivity and high conversion can be attained in this invention by employing the above-mentioned novel catalyst.

This invention will now be illustrated in detail by reference to Referential Examples, Examples and Comparative Examples.

Referential Example 1

This Referential Example is given to illustrate the preparation of a catalyst precursor.

Nickel nitrate, magnesium nitrate and aluminum nitrate were mixed with each other in water to form an aqueous solution (A) containing 0.27 mole/l of Ni(NO$_3$)$_2$; 0.29 mole/l of Mg(NO$_3$)$_2$ and 0.2 mole/l of Al(NO$_3$)$_3$.

Separately, an aqueous solution (B) containing 0.15 mole/l of Na$_2$CO$_3$ and 2 moles/l of NaOH was prepared.

Both the solutions were fed by a metering pump to a 1-liter capacity cylindrical reaction vessel equipped with a stirrer and an overflow device, in which 700 ml of pure water had been charged in advance. The feed rate of the solution (A) was adjusted to 40 ml/min, and the feeding of the solution (B) was so controlled that the pH of the reaction suspension was 9 to 10 as measured at room temperature. After 60 minutes had passed from the initiation of the reaction, the reaction suspension overflown from the reaction vessel was recovered and water was removed therefrom. The remaining solid was washed with water and dried to obtain a catalyst prescursor No. 1 having a composition indicated in Table 1 given hereinbefore. The X-ray diffraction pattern of this precursor was as follows:

| d(A) | I/Io |
|---|---|
| 7.76 | 100 |
| 3.82 | 40 |
| 2.56 | 50 |

This precursor was dried and calcined at 150°C. for 24 hours to remove water of crystallization therefrom. Then, this precursor was used for formation of a catalyst, which will be described hereinafter.

Referential Example 2

Procedures of Referential Example 1 were repeated except that the following changes were made. Thus were obtained catalyst precursors Nos. 2 to 5 shown in Table 1.

Precursors Nos. 2 and 5:

The composition of the aqueous solution (A) was changed as follows:

|  | Precursor No. 2 | Precursor No. 5 |  |
|---|---|---|---|
| Concentration of Ni(NO$_3$)$_2$ | 0.1 mole/l | 0.33 mole/l |  |
| Concentration of Mg(NO$_3$)$_2$ | 0.5 mole/l | 0 mole/l | 0 mole/l |
| Concentration of Al(NO$_3$)$_3$ | 0.4 mole/l | 0.6 mole/l |  |

The so formed precursors had the following X-ray diffraction patterns:

| Precursor No. 2 | | Precursor No. 5 | |
|---|---|---|---|
| d (A) | I/Io | d (A) | I/Io |
| 7.68 | 100 | 7.62 | 100 |
| 3.81 | 50 | 3.76 | 50 |
| 2.53 | 50 | 2.56 | 50 |

Precursors Nos. 3 and 4:

All of water used was replaced by ion-exchanged water, and a solution formed by dissolving NaOH at a concentration of 2 moles/l in ion-exchanged water was used instead of the solution (B). In order to prevent carbon dioxide gas in air from being introduced into the reaction vessel, the preliminary operation and reaction operation were conducted in a nitrogen atmosphere.

The composition of the aqueous solution (A) was changed as follows:

|  | Precursor No. 3 | Precursor No. 4 |
|---|---|---|
| Concentration of Ni(NO$_3$)$_2$ | 0.5 mole/l | 0.33 mole/l |
| Concentration of MgCl$_2$ | 0.15 mole/l | 0 mole/l |
| Concentration of Al(NO$_3$)$_3$ | 0.1 mole/l | 0.2 mole/l |

The soformed precursors had the following X-ray diffraction patterns:

| Precursor No. 3 | | Precursor No. 4 | |
|---|---|---|---|
| d (A) | I/Io | d (A) | I/Io |
| 8.78 | 100 | 8.11 | 100 |
| 4.37 | 30 | 3.98 | 40 |
| 2.80 | 30 | 2.59 | 40 |

Example 1

The catalyst precursor No. 1 was charged in a Pyrex glass reaction tube having an inner diameter of 13 mm and a length of 600 mm in such a manner that the precursor was packed in the central portion of the reaction tube along about 4 cm, and the precursor was reduced at 500°C. for 2 hours by feeding hydrogen at a rate of 12 l/hr. Then, the temperature was lowered to a desired reaction temperature (100, 120° or 150°C.) while continuing the feeding of hydrogen. At this desired reaction temperature, reduction of acetone was carried out at an acetone flow rate of 5.4 ml/hr and a time factor (W/F) of 15 g catalyst.hr/mole. When the reduction was continued for 20 minutes, at each reaction temperature the conversion of acetone was 99 % and the selectivity to isopropanol (IPA) was 100 %. The same results were obtained when the reaction was continued for 150 minutes from the start of the reaction.

The determination of the conversion and selectivity was performed by gas chromatography in this Example and all of Examples given hereinafter.

EXAMPLE 2

In the same manner as described in Example 1, the precursor No. 1 was reduced and calcined at 500°C. for 2 hours. Then, with use of the so treated product, reduction of benzene to cyclohexane was conducted in the same manner as described in Example 1 except that the benzene feed rate was adjusted to 5.4 ml/hr or 10.8 ml/hr and the hydrogen feed rate was adjusted to 12 l/hr or 24 l/hr. Results are shown in Table 2 given below.

marks " ● " and the selectivity is shown by the curve indicated by marks "o".

In this Example, when the reaction temperature was maintained at a level not exceeding 150°C., the activity of the catalyst was hardly lowered even after the reaction was continued for 200 minutes.

EXAMPLE 4

Figure 2:
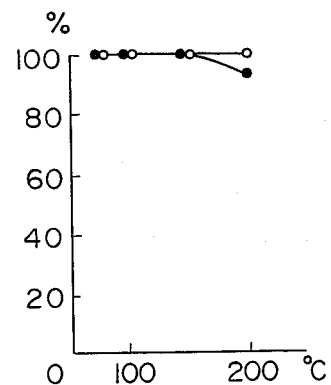
FIG. 2 is a curve illustrating the same relation in the hydrogenation reduction conducted by using the catalyst of Example 4.

In the same manner as described in Example 3, the reduction and calcination of the precursor substance and the reduction of benzene to cyclohexane were carried out except that the catalyst precursor No. 5 was employed instead of the precursor No. 3 used in Example 3. Results are shown in FIG. 2. Even after the reaction was continued for 200 minutes, degradation of the catalyst activity was hardly observed.

Comparative Example 1 preparation of Ni-Al Coprecipitate Catalyst:

According to the method disclosed in Kiyoshi Morikawa et al, "Kogyo Kagaku Zasshi, 64 (5), page 898 (1961)", the catalyst was prepared. More specifically, 300 g of $Al(NO_3)_3.9H_2O$ was dissolved in 1 of water. Separately, 20.1 g of $Ni(NO_3)_2.6H_2O$ was dissolved in 100 cc of water. Both the solutions were mixed, and the mixture was heated at about 70°C. Then, 500 cc of aqueous ammonia containing 28 % by weight of $NH_3$ was gradually added dropwise to the above heated mixture. The resulting faintly blue precipitate was recovered by filtration, washed with water, and molded, dried, and calcined according to customary procedures. Thus was obtained a comparative catalyst precursor having a nickel content of about 10 %.

Table 2

| Reaction Temperature (°C.) | $H_2/C_6H_6$ Mole Ratio | Feed Rate of $C_6H_6$ | Time Factor (W/F) | 10 to 20 Minutes From Initiation of Reaction | | 50 Minutes From Initiation of Reaction | |
|---|---|---|---|---|---|---|---|
| | | | | Selectivity | Conversion | Selectivity | Conversion |
| 100 | 8.0 | 5.4 ml/hr | 18 | 100 % | 100 % | 100 % | 100 % |
| 200 | 8.0 | 5.4 ml/hr | 18 | 100 % | 95 % | 100 % | 95 % |
| 250 | 8.0 | 5.4 ml/hr | 18 | 100 % | 29 % | 100 % | 31 % |
| 100 | 8.0 | 10.8 ml/hr | 9 | 100 % | 97 % | 100 % | 99 % |
| 100 | 4.0 | 10.8 ml/hr | 9 | 100 % | 98 % | 100 % | 99 % |
| 200 | 4.0 | 10.8 ml/hr | 9 | 100 % | 50 % | 100 % | 50 % |

EXAMPLE 3

Figure 5:
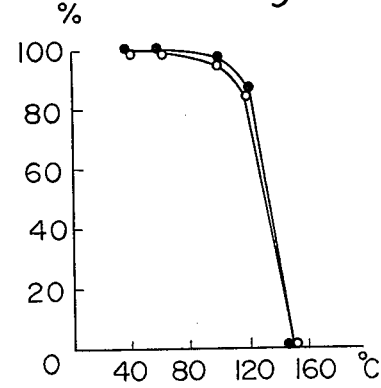
FIG. 5 is a curve illustrating the same relation in the hydrogenation reduction conducted by using the catalyst of Example 5.

The catalyst precursor No. 4 was charged in a Pyrex glass reaction tube having an inner diameter of 13 mm and a length of 600 mm in such a manner that the precursor was packed in the central portion of the tube along 3 cm, and the precursor was reduced at 350°C. for 1 hour in a hydrogen stream fed at a rate of 2 l/hr. The temperature was lowered to a desired reaction temperature while continuing the feeding of hydrogen. At this desired reaction temperature the reduction of benzene was carried out at a benzene flow rate of 5.4 ml/hr, a time factor (W/F) of about 18 g catalyst.hr/mole and a $H_2/C_6H_6$ mole ratio of 8.0. Results obtained at the point when 10 minutes passed from the initiation of the reaction are shown in FIG. 5.

Figure 3:
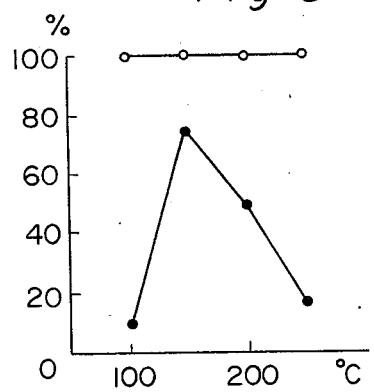
FIG. 3 is a curve illustrating the same relation in the hydrogenation reduction conducted by using the catalyst of Comparative Example 1.

In each of accompanying FIGS. 1 to 5, the abscissa indicates the reaction temperature and the ordinate indicates the conversion (%) and selectivity (%), where the conversion is shown by the curve indicated by Reducton of Benzene to Cyclohexane:

The so formed catalyst precursor was dried at 200°C. for 1 hour, calcined at 400°C. for 2 hours and reduced at 400°C. for 2 hours in a hydrogen stream. Then, the hydrogenation of benzene was conducted with use of the resulting catalyst at a hydrogen/benzene mole ratio of 8.0 and a time factor (W/F) of 65 g catalyst.hour/mole. Results obtained when 15 minutes passed from the initiation of the hydrogenation are shown in FIG. 3.

Comparative Example 2

Figure 4:
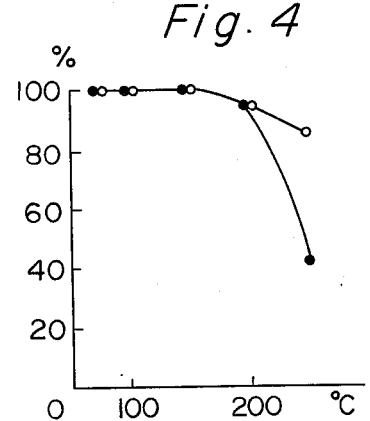
FIG. 4 is a curve illustrating the same relation in the hydrogenation reduction conducted by using the catalyst of Comparative Example 2.

In the same manner as described in Comparative Example 1 a catalyst precursor was prepared except that the Ni/Al atomic ratio was changed to 0.35, and the resulting catalyst precursor was dried, calcined and reduced under the same conditions as described in Comparative Example 1. Then, with use of the so formed catalyst, hydrogenation of benzene was conducted at a hydrogen/benzene mole ratio of 8.0 and a time factor (W/F) of 60 g catalyst.hour/mole. Results obtained at the point when 15 minutes passed from the initiation of the reaction are shown in FIG. 4.

EXAMPLE 5

With use of the same catalyst and reaction vessel as employed in Example 3, reduction of acetone to isopropanol was conducted at a hydrogen/acetone mole ratio of 6.0 and a time factor (W/F) of 14 g catalyst.hr./mole. Results obtained are shown in FIG. 5. When the reaction was carried out at a temperature not exceeding 120°C., the degradation of the catalyst activity was not observed even after the reaction was continued for 200 minutes.

EXAMPLE 6

2 g of the same reduction catalyst as used in Example 3 was charged together with 200 g of phenol into a 1-l inner capacity autoclave, and air was replaced by hydrogen. Reduction of phenol to cyclohexanol was carried out at 150°C. under agitation while controlling the hydrogen pressure to 100 Kg/cm$^2$. Absorption of hydrogen was completed in 35 minutes from the initiation of the reduction, and the conversion of phenol was 100 % and the selectivity to cyclohexanol was 100 %.

Example 7

The catalyst precursor No. 3 was calcined and reduced in the same manner as described in Example 3 except that the reduction temperature was adjusted to 500°C. and the reduction was conducted for 2 hours. With use of this catalyst and the same reaction vessel as employed in Example 3, hydrogenation reduction of butylaldehyde to n-butanol was carried out under the same conditions as employed in Example 3 except that the reaction temperature was changed as indicated below. Results obtained at the point when the reaction was continued for 20 minutes are as follows:

| Reaction Temperature (°C.) | Conversion (%) | Selectivity (%) |
|---|---|---|
| 150 | 100 | 100 |
| 200 | 100 | 100 |

EXAMPLE 8

The catalyst precursor No. 4 was calcined and reduced under the same conditions as described in Example 3. With use of the so formed catalyst and the same reaction vessel as employed in Example 3, hydrogenation reduction of propionaldehyde to n-propyl alcohol was conducted under the same conditions as adopted in Example 3 except that the reaction temperature was changed as indicated below. Results obtained at the point when the reaction was continued for 20 minutes are as follows:

| Reaction Temperature (°C.) | Conversion (%) | Selectivity (%) |
|---|---|---|
| 150 | 98 | 100 |

EXAMPLE 9

The catalyst precursor No. 4 was calcined and reduced under the same conditions as adopted in Example 3. With use of the so obtained catalyst and the same reaction vessel as employed in Example 3, hydrogenation of hexene-1 to n-hexane was conducted under the same conditions as adopted in Example 3 except that the reaction temperature was changed as indicated below. Results obtained at the point when the reaction was continued for 20 minutes are as follows:

| Reaction Temperature (°C.) | Conversion (%) | Selectivity (%) |
|---|---|---|
| 100 | 95 | 98 |
| 150 | 98 | 100 |

EXAMPLE 10

The catalyst precursor No. 4 was calcined and reduced under the same conditions as described in Example 3, and with use of the so formed catalyst and the same reaction vessel as employed in Example 3, hydrogenation of iso-octene to iso-octane was carried out under the same conditions as adopted in Example 3 except that the reaction temperature was changed as indicated below. Results obtained at the point when the reaction was continued for 20 minutes are shown below.

| Reaction Temperature (°C.) | Conversion (%) | Selectivity (%) |
|---|---|---|
| 100 | 95 | 100 |
| 150 | 82 | 96 |
| 200 | 73 | 96 |

EXAMPLE 11

The catalyst precursor No. 2 was calcined and reduced under the same conditions as adopted in Example 3, and with use of the so formed catalyst and the same reaction vessel as employed in Example 6, hydrogenation reduction of cinnamyl alcohol to hydroxycinnamyl alcohol (p-phenylpropyl alcohol) under the same conditions as adopted in Example 6 except that the reaction temperature was changed as indicated below and tetrahydrofuran was used as a solvent. Results obtained at the point when the reaction was continued for 40 minutes are as follows:

| Reaction Temperature (°C.) | Conversion (%) | Selectivity (%) |
|---|---|---|
| 100 | 98 | 100 |
| 150 | 98 | 100 |

EXAMPLE 12

The catalyst precursor No. 5 was calcined and reduced under the same conditions as described in Example 3, and with use of the resulting catalyst and the same reaction vessel as employed in Example 6, hydrogenation reduction of phenylacetaldehyde to phenylethyl alcohol was carried out under the same conditions as adopted in Example 6 except that the reaction temperature was changed as indicated below and ethanol was used as a solvent. Results obtained at the point when the reaction was continued for 20 minutes are as follows:

| Reaction Temperature (°C.) | Conversion (%) | Selectivity (%) |
|---|---|---|
| 150 | 95 | 99 |

EXAMPLE 13

The catalyst precursor No. 4 was calcined and reduced under the same conditions as described in Example 3, and with use of the resulting catalyst and the same reaction vessel as employed in Example 3, hydrogenation reduction of butylmethylketone to butylmethylcarbinol (2-hexanol) was carried out under same conditions as adopted in Example 3 except that the reaction temperature was changed as indicated below. Results obtained at the point when the reaction was continued for 20 minutes are as follows:

| Reaction Temperature (°C.) | Conversion (%) | Selectivity (%) |
|---|---|---|
| 150 | 91 | 99 |
| 200 | 85 | 99 |

EXAMPLE 14

The catalyst precursor No. 4 was reduced in the same manner as described in Example 1. 2 g of the resulting catalyst was charged together with 150 g of diphenyl into a 1-liter capacity autoclave, and the inside atmosphere was replaced by hydrogen. The reaction was conducted under agitation at a temperature maintained at 200°C. while controlling the hydrogen pressure to 80 atmospheres. Absorption of hydrogen was completed in 30 minutes from the initiation of the reaction. The resulting reaction product comprised as main products 15 % of cyclohexyl benzene and 80 % dicyclohexyl.

EXAMPLE 15

The catalyst precursor No. 4 was calcined and reduced under the same conditions as described in Example 3, and with use of the resulting catalyst and the same reaction vessel as employed in Example 6, hydrogenation reduction of adiponitrile to hexamethylene diamine was carried out under the same conditions as employed in Example 6 except that the reaction temperature was changed as indicated below and ammonia was filled in the autoclave. Results obtained at the point when the reaction was continued for 40 minutes are as follows:

| Reaction Temperature (°C.) | Conversion (%) | Selectivity (%) |
|---|---|---|
| 100 | 98 | 99 |

Referential Example 3

A catalyst precursor No. 6 of the following composition

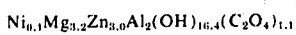

was prepared in the same manner as described in Referential Example 1 except that the following changes were made.

An aqueous solution having the following composition was employed instead of the aqueous solution (A):

| | |
|---|---|
| Ni(NO$_3$)$_2$ | 0.1 mole/l |
| MgCl$_2$ | 0.3 mole/l |
| Zn(NO$_3$)$_2$ | 0.3 mole/l |
| Al(NO$_3$)$_3$ | 0.2 mole/l |

A solution prepared by dissolving NaOH at a concentration of 3 moles/l and oxalic acid (COOH) at a concentration of 0.3 mole/l into ion-exchanged water was used instead of the aqueous solution (B). The X-ray diffraction pattern of the resulting catalyst precursor was as follows:

| d (A) | I/Io |
|---|---|
| 9.43 | 100 |
| 4.71 | 40 |
| 3.17 | 35 |

The specific surface area and the X-ray particle size of the product obtained by calcining and reducing the above precursor were as follows:

| Reducing Conditions | BET Specific Surface Area | X-ray Particle Size |
|---|---|---|
| I | 278 m²/g | too fine and immesurable |
| II | 243 m²/g | too fine and immesurable |

EXAMPLE 16

With use of the catalyst precursor obtained in Referential Example 3, reduction of the precursor and reduction of benzene to cyclohexane were carried out in the same manner as described in Example 2 except that the reaction temperature was changed as indicated below. The following results were obtained:

| Reaction Temperature (°C.) | Conversion (%) | Selectivity (%) |
|---|---|---|
| 50 | 40 | 100 |
| 100 | 40 | 100 |
| 150 | 30 | 100 |

Referential Example 4

A catalyst precursor No. 7 expressed by the following composition formula

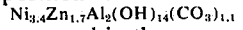

was prepared in the same manner as described in Referential Example 1 except that the following changes were made. An queous solution of the following composition was employed instead of the aqueous solution (A):

| | |
|---|---|
| NiC$_2$ | 0.8 mole/l |
| ZnC$_2$ | 0.4 mole/l |
| AlC$_3$ | 0.2 mole/l |

The X-ray diffraction pattern of the resulting precursor was as follows:

| d (A) | I/Io |
|---|---|
| 7.82 | 100 |
| 3.79 | 30 |
| 2.59 | 30 |

The specific surface area and X-ray particle size of the reduction product formed from the above precursor were as follows:

| Reducing Conditions | BET Specific Surface Area | X-ray Particle Size |
|---|---|---|
| 12 l/hr of H, 300°C., 2 hours | 153 m²/g | too fine and immesurable |
| 1 | 131 m²/g | too fine and immesurable |

EXAMPLE 17

With use of the catalyst precursor No. 7, a catalyst was prepared in the same manner as described in Example 1 except that the calcination reduction temperature was adjusted to 500°C. With use of the so formed catalyst, reduction of acetone was carried out under the same conditions as employed in Example 1. Results obtained at the point when the reaction was continued for 10 minutes are as follows:

| Reaction Temperature (°C.) | Conversion (%) | Selectivity (%) |
|---|---|---|
| 100 | 99 | 100 |

EXAMPLE 18

The catalyst precursor No. 5 was pulverized to have a size less than 90 mesh and was reduced at a feed rate of 10 g/hr in a stainless steel rotary kiln having a length of 1000 mm and an inner diameter of 100 mm in a hydrogen stream. The residence time of the precursor was 3 hours. The so reduced product was fed into a molten hardened oil without contacting it with air. The resulting flaky catalyst was added to 300 g of a rorqual oil having an iodine value of 122 in such an amount that the nickel content was 0.2 %. The oil was charged in a 1-liter inner capacity autoclave being rotated at 1000 rpm, and air was replaced by hydrogen. Hydrogenation was carried out at 180°C. under agitation while controlling the hydrogen pressure to 2 Kg/cm². Absorption of hydrogen was completed in 25 minutes from the initiation of the reaction. The resulting hardened oil had a melting point of 67°C. and an iodine value of 0.5.

EXAMPLE 19

The same flaky catalyst as employed in Example 18 was added to 300 g of a soybean oil having an iodine value of 130 and a fatty acid composition of 10 % of palmitic acid, 4 % of stearic acid, 24 % of oleic acid, 53 % of linoleic acid and 9 % of linolenic acid, in such an amount that the Ni content was 0.1 %. The oil was charged into a 1-liter inner capacity autoclave being rotated at 1200 rpm, and air was replaced by hydrogen. Hydrogenation was conducted at 160°C. under agitation for 12 minutes while controlling the hydrogen pressure at 1.8 Kg/cm². As a result, there was obtained a hardened oil having an iodine value of 71, a melting point of 42°C. and a fatty acid concentration of 10 % of palmitic acid, 13 % of stearic acid and 77 % of oleic acid.

What we claim is:

1. A process for hydrogenation of organic compounds which comprises reducing with hydrogen an unsaturated organic compound wherein the organic compound is a carbonyl compound expressed by the following formula $$R-\underset{\underset{O}{\|}}{C}-R^1 \quad \text{or} \quad R-\underset{\underset{O}{\|}}{C}-O-R^2$$

wherein R is an alkyl or aralkyl group having up to 12 carbon atoms, $R^1$ stands for a hydrogen atom or the group R, and $R^2$ stands for a lower alkyl group having up to 4 carbon atoms.

in the presence of a solid catalyst for reduction, wherein the solid reduction catalyst consists essentially of a product obtained by calcining and reducing at a temperature of 350° to 700°C. in a hydrogen stream a precursor compound having a composition expressed by the following general formula $$M_xNi_yAl_z(OH)_{2x+2y+3z-tp}(A)_p \cdot aH_2O$$

wherein A stands for an anion, M stands for at least one metal selected from the group consisting of magnesium and zinc, $t$ designates the valency of the anion A, and $x$, $y$, $z$, $p$ and $a$ are such numbers that when $z$ is 2, the following relations are established:
$x + y = 0.1$ to 20,
$x = 0$ to 19.9, and
$y = 0.1$ to 20
and the following conditions are satisfied:
$1/6 > p/(x + y + z) > 1/20$, and
$a > 0$
and having substantially the following diffraction pattern in the powder X-ray diffractiometry (Cu-K$\alpha$)

| d (Å) | I/Io |
|---|---|
| 7.5 – 21.02 | 100 |
| 3.6 – 10.6 | 5 – 80 |
| 2.4 – 6.4 | 5 – 60 |

2. A process according to claim 1 wherein the anion A in the precursor compound is selected from the group consisting of halide ions, nitric acid ion, carbonic acid ion, formic acid ion and oxalic acid ion.

3. A process according to claim 1 wherein the solid reduction catalyst has a BET specific surface area of at least 100 m²/g and an X-ray particle size on (111) face not exceeding 60 Å.

4. A process according to claim 1 wherein the precursor compound has a composition expressed by the following formula
$$Ni_yAl_2(OH)_{6+2y-tp}(A)_p \cdot aH_2O$$
wherein A stands for a nitric acid ion, a formic acid ion, oxalic acid ion or a carbonic acid ion, y is a number of from 0.1 to 6, $t$ designates the valency of the anion A, $a$ is a positive number, and $p$ is a number satisfying the condition of $1/6 > p/(2+y) > 1/20$.

5. A process according to claim 1 wherein the precursor compound has a composition expressed by the following formula
$$Ni_yMg_xAl_2(OH)_{6+2y+2x-tp}(A)_p \cdot aH_2O$$
wherein A is a nitric acid ion, a formic acid ion, an oxalic acid ion or a carbonic acid ion, y is a number of from 0.1 to 10, x is a number of from 1.5 to 5.5, $t$ designates the valency of the anion A, $a$ is a positive number, and $p$ is a number satisfying the condiiton of $1/6 > p/(2+y+x) > 1/20$.

6. A process according to claim 1 wherein the precursor compound has a composition expressed by the following formula
$$Ni_yZn_xAl_2(OH)_{6+2y+2x-tp}(A)_p \cdot aH_2O$$

wherein A is a nitric acid ion, a formic acid ion, an oxalic acid ion or a carbonic acid ion, $y$ is a number of from 0.1 to 10, $x$ is a number of from 1.5 to 5.5, $t$ designates the the valency of the anion A, $a$ is a positive number, and p is a number satisfying the condition of $1/6 > p/(2+y+x) > 1/20$.

7. A process according to claim 1 wherein the precursor compound has a composition expressed by the following formula

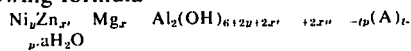
$\cdot aH_2O$ wherein A is a nitric acid ion, a formic acid ion, an oxalic acid ion or carbonic acid ion, $y$ is a number of from 0.1 to 10, $x'$ and $x''$ each stand for a number of from 1.5 to 5.5, $t$ designates the valency of the anion A, $a$ is a positive number, and $p$ is a number satisfying the condition of $1/6 > p/(2+y+x'+x'') > 1/20$.

8. A process according to claim 1 wherein the mole ratio of nickel oxide (NiO) : metallic nickel in the catalyst is within a range of from 30 : 70 to 97 : 3.

9. A process according to claim 1 wherein the hydrogenation is carried out at a temperature ranging from room temperature to 250°C.

10. A process according to claim 1 wherein the hydrogenation is carried out in the presence of hydrogen maintained at a pressure ranging from atmospheric pressure to 500 Kg/cm².

11. The process of claim 1 wherein said carbonyl compound is selected from the group consisting of acetone, methylethylketone, butylaldehyde, phenylacetaldehyde and ethylphenylacetate.

* * * * *

UNITED STATES PATENT OFFICE
CERTIFICATE OF CORRECTION

Patent No. 3,932,534            Dated January 13, 1976

Inventor(s) FUKUNAGA, ET AL.

It is certified that error appears in the above-identified patent and that said Letters Patent are hereby corrected as shown below:

Item 73, line 2, delete "Kaishi", insert -- Kaisha --

Claim 5, line 5, delete ", a" (in italics), insert -- , a --

Claim 7, line 4, delete "$Mg_x$", insert -- $Mg_{x''}$ --

Column 22, line 1, delete "$(2+y+x'+x'\lambda$", insert
        -- $(2+y+x'+x'') > 1/20.$ --

Column 22, line 2, delete in its entirety.

$\mathfrak{Signed}$ and $\mathfrak{Sealed}$ this

*twenty-fifth* $\mathfrak{Day}$ of *May 1976*

[SEAL]

Attest:

RUTH C. MASON            C. MARSHALL DANN
*Attesting Officer*        *Commissioner of Patents and Trademarks*